United States Patent
Galdi

(10) Patent No.: US 12,300,372 B2
(45) Date of Patent: May 13, 2025

(54) BIO-DATA INFORMED SUPPLEMENT SUPPLY SYSTEM

(71) Applicant: Helo Corp., San Francisco, CA (US)

(72) Inventor: Fabio Galdi, Santa Clara, CA (US)

(73) Assignee: Helo Corp., San Francisco, CA (US)

( * ) Notice: Subject to any disclaimer, the term of this patent is extended or adjusted under 35 U.S.C. 154(b) by 353 days.

(21) Appl. No.: 17/308,239

(22) Filed: May 5, 2021

(65) Prior Publication Data

US 2022/0359053 A1 Nov. 10, 2022

(51) Int. Cl.
*G16H 20/13* (2018.01)
*G06N 20/00* (2019.01)
*G16H 20/60* (2018.01)

(52) U.S. Cl.
CPC .............. *G16H 20/13* (2018.01); *G06N 20/00* (2019.01); *G16H 20/60* (2018.01)

(58) Field of Classification Search
CPC ........ G16H 20/13; G16H 20/10; G16H 20/60; G16H 10/60
See application file for complete search history.

(56) References Cited

U.S. PATENT DOCUMENTS

| 2016/0158107 A1* | 6/2016 | Dvorak | A61J 7/0084 221/9 |
| 2018/0028408 A1* | 2/2018 | Li | A61J 7/0445 |
| 2019/0339006 A1 | 11/2019 | Cronin | |
| 2021/0205180 A1* | 7/2021 | Pugsley | G16H 20/13 |
| 2021/0249112 A1* | 8/2021 | Mercolino | A61J 7/0053 |

FOREIGN PATENT DOCUMENTS

| WO | WO-2019055545 A1 * | 3/2019 | A61J 7/0076 |
| WO | 2019246629 | 12/2019 | |

OTHER PUBLICATIONS

Yang, Geng, et al. "A health-IoT platform based on the integration of intelligent packaging, unobtrusive bio-sensor, and intelligent medicine box." IEEE transactions on industrial informatics 10.4 (2014): 2180-2191. (Year: 2014).*
PCT International Search Report and Written Opinion for International Application No. PCT/US22/27749, Sep. 2, 2022, 8 pages.

* cited by examiner

*Primary Examiner* — Jason B Dunham
*Assistant Examiner* — Constantine Siozopoulos
(74) *Attorney, Agent, or Firm* — Nikitas E. Nicolakis; Lombard & Geliebter LLP

(57) ABSTRACT

The present application provides a personal supplement supply system that includes: a delivery device, which further includes a housing having a plurality of cartridges removably attached to a base located within the housing. Each of the plurality of cartridges store therein at least one dispensable ingredient. The device includes a processor coupled to computer memory, the computer memory having software stored thereon that when executed causes the delivery device to dispense the at least one dispensable ingredient from each of the plurality of cartridges in accordance with a bio-informed plan personalized for a user of the delivery device.

25 Claims, 13 Drawing Sheets

BIO-DATA INFORMED SUPPLEMENT SUPPLY SYSTEM

FIELD OF THE APPLICATION

The present application relates generally to a supplement supply system, and more particularly to a supplement supply system designed to deliver one or more personalized daily doses of dietary and other nutritional supplements.

BACKGROUND OF THE APPLICATION

Consumers purchase a wide variety of supplements to support their health objectives. Often, consumers will mix and match various combinations of supplements according to factors, such as their mood, time of day, health objectives, or in advance of or following certain activities, all typically based on certain perceived recommended standardized allowances. This way of taking supplements, however, does not account for the individualized needs of the consumer at a given time. Rather, recommended allowances may be suggestions for the average consumer. Individuals that have certain nutritional deficiencies or that are more active than the average consumer may therefore consume an insufficient dose of a supplement. Similarly, an underactive individual may overconsume supplements. The current way for dosing dietary supplements therefore fails to account for the user's specific nutritional supplement needs. Accordingly, there is a need for a personal supplement supply system that is not so limited.

SUMMARY OF THE APPLICATION

The present application provides a personal supplement supply system that includes: a delivery device, which further includes a housing having a plurality of cartridges removably attached to a base located within the housing, each of the plurality of cartridges storing therein at least one dispensable ingredient; and a processor coupled to computer memory, the computer memory having software stored thereon that when executed causes the delivery device to dispense the at least one dispensable ingredient from each of the plurality of cartridges in accordance with a bio-informed plan personalized for a user of the delivery device.

In at least one embodiment, the ingredient includes at least one dietary supplement.

In at least one embodiment, each of the plurality of cartridges store the dispensable ingredient in a plurality of blister packs and wherein each of the plurality of cartridges are configured to be refilled with blister packs.

In at least one embodiment, at least one of the plurality of cartridges or the plurality of blister packs are addressed with a code, and wherein the delivery device is configured to recognize ingredients in blister packs and track consumption thereof based on said code.

In at least one embodiment, the delivery device further includes a communication unit, the delivery device therewith operable to communicate with at least one mobile device over a communication network and receive therefrom user specific biometric data, wherein the personalized bio-informed plan is determined based at least in part on the user specific biometric data received from the mobile device.

In at least one embodiment, the user specific biometric data includes objective health data.

In at least one embodiment, the user specific biometric data includes subjective health data.

In at least one embodiment, the software when executed further causes the delivery device track consumption by the user of the at least one dispensable ingredient and update the bio-informed plan personalized based on said consumption and based on changes to user specific biometric data after a start of said consumption.

In at least one embodiment, at least one of the mobile device or the delivery device are operable to communicate biometric data to a remote server and wherein the remote server communicates the personalized bio-informed plan determined based on the biometric data by the server to the delivery device.

In at least one embodiment, the server executes an artificial intelligence cloud service and wherein the cloud service determines the personalized bio-informed plan based on biometric reports from a plurality of users and a correlation of changes to biometric data with ingredient consumption.

In at least one embodiment, the delivery device is operable to receive a request for a supplement via the delivery device, communicate the request to the server, and receive from the server the personalized bio-informed plan for the user in response to the request for the supplement.

In at least one embodiment, the software when executed further causes the delivery device to track consumption by the user of the at least one dispensable ingredient, and wherein the bio-informed plan is personalized in real-time based on said consumption and based on changes to user specific biometric data over a preceding time period.

In at least one embodiment, the base includes a carousel rotatable about an opening in the base, wherein the software when executed aligns an opening in a first one of the plurality of cartridges to a dispensing mechanism for dispensing a first ingredient and aligns an opening in a second of the plurality of cartridges to the dispensing mechanism for dispensing a second ingredient, the first and second ingredients dispensed based on the bio-informed plan.

In at least one embodiment, the delivery device includes a removable cup aligned with the opening in the base for receiving a mixture includes the first and second ingredients.

In at least one embodiment, the supplemental supply system includes a rail slidably coupled to the housing, the cup removably attached to the rail.

In at least one embodiment, each of the plurality of cartridges include at least one blister pack and wherein the dispensing mechanism includes armature that feeds blister packs over the opening in the base.

In at least one embodiment, the opening in the base includes at least one blade, the dispensing mechanism includes a hammer mechanism that presses the at least one blister pack onto the at least one blade for cutting the blister pack and releasing ingredients therefrom into a cup.

In at least one embodiment, the dispensing mechanism includes a retention plate pivotally coupled to the base, the retention plate having an opening therein that coincides with the opening in the base and a plurality alignment pins that align blister packs fed thereto over the opening in the retention plate, the retention plate operable to eject spent blister packs into a drawer located within the housing.

In another aspect, a personal supplement supply system is provided that includes a delivery device, the delivery device includes a housing having a plurality of refillable cartridges removably attached to a base located within the housing, each of the plurality of cartridges storing therein at least one dispensable ingredient in a blister pack; a processor coupled to computer memory, the computer memory having software stored thereon that when executed causes the delivery device to: dispense the at least one dispensable ingredient from each of the plurality of cartridges in accordance with a bio-informed plan personalized for a user of the delivery device, track consumption by the user of at least first and second dispensable ingredients; and a communication unit, the delivery device therewith operable to: communicate with at least one mobile device over a communication network and receive therefrom user specific biometric data, communicate with at least one server the user specific biometric data and said consumption, wherein the personalized bio-informed plan is determined based at least in part on the user specific biometric data, and received from the at least one server for execution bio-informed updated bio-informed plans based on said consumption.

In at least one embodiment, the base includes a carousel rotatable about an opening in the base, wherein the software when executed aligns an opening in a first one of the plurality of cartridges to a dispensing mechanism for dispensing the first ingredient and aligns an opening in a second of the plurality of cartridges to the dispensing mechanism for dispensing the second ingredient, the first and second ingredients dispensed based on the bio-informed plan.

In at least one embodiment, the supplemental supply system includes a rail slidably coupled to the housing and a cup for receiving dispensed ingredients removably attached to the rail.

In at least one embodiment, each of the plurality of cartridges include at least one blister pack and wherein the dispensing mechanism includes armature that feeds blister packs over the opening in the base.

In at least one embodiment, the opening in the base includes at least one blade, the dispensing mechanism includes a hammer mechanism that presses the at least one blister pack onto the at least one blade for cutting the blister pack and releasing ingredients therefrom into a cup.

In at least one embodiment, the dispensing mechanism includes a retention plate pivotally coupled to the base, the retention plate having an opening therein that coincides with the opening in the base and a plurality alignment pins that align blister packs fed thereto over the opening in the retention plate, the retention plate operable to eject spent blister packs into a drawer located within the housing.

Other objects and features of the disclosures of the present application will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, where like reference characters denote corresponding or similar elements throughout the various figures.

DETAILED DESCRIPTION OF PREFERRED EMBODIMENTS

Figure 1:
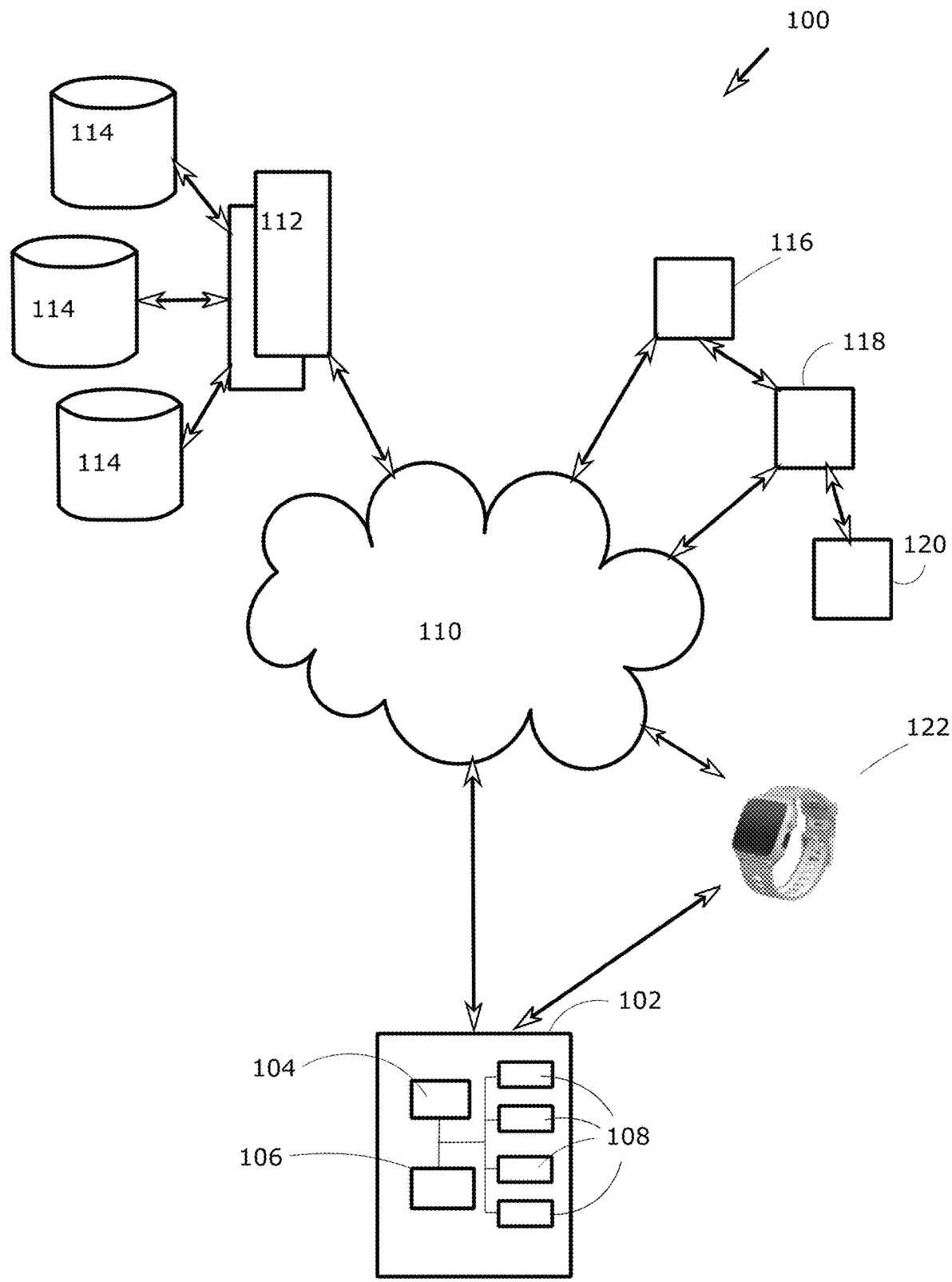
FIG. 1 illustrates a personal supplement supply system in a communication network in accordance with an exemplary embodiment of the systems disclosed herein.

In various exemplary embodiments thereof, the supplement supply system of the present application, which may be referred to as the NutraMatic™, addresses and resolves one or more of the drawbacks of previously known supplement supply systems, while at the same time providing significant additional benefits and advantages.

In this regard, a supplement supply system is provided that delivers single or multiple daily doses of one or more dietary supplements on demand, considering the individualized needs of the consumer at the time of consumption. The term dietary supplement includes, but is not limited to, a vitamin, a mineral, an herb or other botanical, a protein, carbohydrate, fat or oil, an amino acid or other activator, or any other dietary substance, or any combination thereof. Although discussed herein in the context of dietary supplements, the systems disclosed herein may be used for personalized dosage of pharmaceutical compositions or phyto-cannabinoid, such as Cannabidiol, and is therefore not limited thereto. Preferably, the composition and/or the dosage of each of the one or more dietary supplements that make up the dose is determined by a computer system, in real time, based on a report that includes the individual user's biometric data for a certain preceding time period, e.g., prior 24, 12, 8 hours, etc., from the previous reading/supplement delivery, etc., or based on a current reading of the individual user's biometric data, or any combination thereof together with user data from other sources. The report may be generated using any data collection device, i.e., a client device, including a wearable personal healthcare device, such as the devices disclosed in U.S. Pat. No. 10,912,519 and U.S. Patent Application No. 63/088,223 and Ser. No. 17/142,093, which are hereby incorporated herein by reference.

Biometric data used for delivering personal supplements, as discussed herein, may include, but is not limited to, heart rate, respiratory rate, body fat percentage, steps taken or other exercise data, calories burned and/or consumed, ECG/EKG, resting heart rate, blood pressure, body temperature, glucose levels, blood alcohol, blood oxygen, sleep quality, weight, etc. In addition to such objective biometric data, the system may prompt for or otherwise collect from the user subjective biometric data, such as how the user is feeling (e.g., mood or pain scale). Finally, the system may track dietary supplement consumption and correlate the consumption of specific supplements with the biometric data or changes therein.

The computer system may, based on the user's biometrics, determine the composition and/or dosage of each dose of the one or more dietary supplements, thereby accounting for the individual's specific supplement needs. The correlation between the biometrics and supplement composition/dosage may be established in a variety of ways, including using machine learning or other artificial intelligence correlation systems. The topology of the computer system too may vary. For example, the system may be a stand-alone supplement delivery device or preferably a plurality of devices communicatively coupled over a computer network. In a preferred embodiment, the system includes a supplement delivery device coupled to one or more servers over the network. The one or more servers are preferably coupled to one or more biometric data collection devices, such as the personal healthcare devices noted above, over the communications network. In this regard, the biometrics collected via the data collection device may be communicated to the remote servers for, inter alia, machine learning correlations and/or composition/dosage determinations. The supplement delivery device may be connected to the servers over the network, and the delivery device may receive from the servers the composition/dosage determinations and may dispense the supplement accordingly. The delivery device may also provide information to the servers, such as usage information, supplement inventory, etc.

In one aspect, the supplement delivery device includes a set of dietary supplements in dispensable packaging that can be mixed on demand based on the user's preceding biometric report. In one embodiment, the device includes a plurality, e.g., up to 10 or preferably 20, base-group ingredients packed in cartridges, which are loaded directly into the device for mixing and/or dispensing. The system can mix supplements from the base-group, as instructed by the system, to produce personalized combinations and dosage of supplements, which may include a single on-demand dose or multiple daily doses (for example, up to 60 daily doses). The supplements may be provided in different bioavailability formats, such as pills, powders, liquids, etc., both in soluble and non-soluble forms, and as carbonated powders, etc. The system may therefore be able to create a seemingly infinite number of unique dose combinations on demand at the delivery device.

In one embodiment, the ingredients/supplements are available in a refill blister pack (e.g., a 10 or 20 supplement roll), with each pack coded to enable the system to recognize and monitor the quantity of each ingredient stored in the delivery device. The individual blister packs may be loaded into the cartridge for dispensing. In addition, the system can control the dosage dispensed to safely regulate the supply of each specific ingredients based on any daily recommended limits. In addition, each refill pack may be available in multiple flavors (e.g., Green Apple Lime, Orange, Mellon, Cranberry, Coconut and Grape).

In one embodiment, the personalized supplement composition/dosage or "shot" can be prepared in real-time by the delivery device based on the formulation instructions provided to it from the remote server, the server preferably using an online artificial intelligence cloud service (referred to herein as the "AI engine") to determine the personalized formulation on demand. On demand formulations can be prepared using the AI engine, which can be queried by the delivery device or any client device using, for example, voice commands. The AI engine can gather information regarding the user's personal status, retrieve/receive the user's biometric data from the linked devices, and formulate a specific supplement combination/dosage based on information provided to the AI engine and based on certain interactions with the user.

A personalized single "shot" or a schedule of "shots" can be prepared by the system/delivery device according to a variety of data sources, including the user's personal profile created by the user and shared with the system, a DNA, blood, and/or microbiome analysis, the user's responses to health assessment questionnaires/surveys (i.e., subjective biometrics), the user's activity and other objective biometric data, gathered by other devices that are connected via a communication network to the system/delivery device, such as a smartphone, smartwatch, or other wearable device. This data is preferably provided to the AI engine to be compiled and used to perform the functions disclosed herein, including formulating the dosage for the given user.

In one embodiment, the system/delivery device may perform automatic self-checks and/or track the ingredient/supplement levels in the delivery device and automatically send a refill order via a communication network to a service provider for the specific ingredients/supplements that are running low.

Referring to FIG. 1, a personal supplement supply system 100 according to at least one embodiment includes a supplement delivery device 102 having a processor 104 coupled to a computer memory 106. The device 102 generally includes a plurality of receptacles/cartridges 108 each containing a base ingredient/supplement to be dispensed. The cartridges preferably include blister packs containing the ingredients. The processor 104 controls the receptacles/cartridges 108 to dispense personalized supplement formulations (composition/dosage) therefrom. Although the device 102 may be shown and described as a free-standing device, it is understood that the functionality may be implemented in other devices, including a wall-mounted device, or as part of another device with other functionality, or as any other device capable of performing the functionality disclosed herein. The memory 106 stores therein software that when executed causes the device 102 to perform the functions described herein. The processor 104 is preferably further coupled to a transmitter/receiver that enables communication via a network 110 between the device 102 and other devices, as shown and as discussed further below.

The device 102 is preferably operable to communicate with other devices (112, 116, 118, 120, etc.) directly or over the network 110. For instance, device 102 may communicate directly with a mobile device 116, such as a smartphone, smartwatch, tablet, or personal computer, personal healthcare device 122, a smart weight scale, or other data collection device 120, via a short-range wireless connection, such as Bluetooth®. Additionally, the device 102 may be operable to communicate indirectly with these, as well as other devices, over a local LAN or a global network such as the Internet, via a wired and/or wireless medium, including a GSM or LTE connections, or a combination thereof. Finally, the device 102 may operate to provide the functionality discussed herein in conjunction with one or more server computers 112 that are further coupled to one or more databases 114 via the Internet or any other computer network 110. The databases 114 generally store the information discussed herein and provide this data to, e.g., the AI engine, to perform the functions discussed herein.

The network 110 may be any suitable type of network allowing transport of data communications across thereof. The network 110 may couple devices so that communications may be exchanged, such as between servers 112 and client devices (102, 116, 118, 120, 122) or other types of devices, including between wireless devices coupled via a wireless network, for example. A network may also include mass storage, such as network attached storage (NAS), a storage area network (SAN), cloud computing and storage, or other forms of computer or machine readable media, for example. In one embodiment, the network may include the Internet, using known Internet protocols for data communication, or any other communication network, e.g., any local area network (LAN) or wide area network (WAN) connection, cellular network, wire-line type connections, wireless type connections, or any combination thereof. Communications and content stored and/or transmitted to and from client devices may be encrypted using, for example, the Advanced Encryption Standard (AES) with a 256-bit key size, or any other encryption standard known in the art.

The system 100 may include an artificial intelligence cloud service (AI engine). The AI engine generally determines the personalized supplement formulations, preferably remotely, for example, using server(s) 112. In this regard, the servers receive biometric reports from users, such as from devices 102, 116, 118, 120, and 122. The biometric reports are stored in one or more databases 114. The servers 112 provide the personalized service for a plurality of users. In this regard, the databases 114 contain the biometric reports for a plurality of users in association with their personal user accounts/records. These biometric reports may be used to teach a machine learning algorithm and for the algorithm to correlate changes to the user's biometrics based on the user's supplement consumption. This correlation may then be used to create the formulations for on-demand supplement dispensing, as discussed herein. The correlations may be maintained for the individual or for classes of individuals. For example, the same correlations may be used for a class of users that fit certain gender, age, and body fat percentage.

Servers 112, as described herein, may vary widely in configuration or capabilities but are comprised of at least a specifically configured digital computing device including at least one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like. The servers 112 are configured to receive requests from delivery devices 102 or other connected devices and process the requests to generate responses accordingly across the network 110. The requests may include requests to dispense a supplement shot, in response to which the system 100 (e.g., AI engine) will preferably query the applicable devices 102, 116, 118, 120, and 122 for or otherwise access the biometric report(s) for the user for the preceding time (e.g., past 24 hours, etc.) or for the present, or a combination thereof, and formulate the personalized supplement composition and dosage on demand, in real time. The formulation may then be communicated to the delivery device 102, which will mix the formulation according to the instructions from the server and dispense the dose for consumption.

Referring now to FIGS. 2A-2I, an exemplary embodiment for the personal supplement delivery device 102 is shown. The device 102 generally includes a housing 202 made of a top section 204 and a base section 206, which together define the exterior of the device 102. The base section 206 may include feet 208 upon which the device may sit on a surface, one or more power supplies 212, and an on/off switch 214 to activate the device. The device 102 may include an interface, such as a touch screen 210 for the user to interact with the device 102/system 100. Additionally, the device may include various lights that indicate the status of the system, as discussed further below.

As discussed above, the device 102 may include a set of ingredients/supplements, preferably contained in cartridges 220. These ingredients/cartridges are maintained within the housing 202 of the device, preferably in the top section 204. In this regard, the housing section 204 may include one or more openings/doors that provide access to the ingredients/cartridges, such as door 218, removable from the section 204 as shown in FIG. 2F to provide access to the ingredient cartridges 220. The top section 204 may be removable from the base section 206, as shown in FIG. 2D, by depressing release buttons 224.

In a preferred embodiment, a first opening is provided on the front exterior surface of the base 206. The opening 216 provides access to the interior space of the device and further provides a means for accessing supplement doses mixed and dispensed by the system 100. The opening 216 according to one embodiment is reversibly closable compartment, for example, by means of a sliding drawer 216. The drawer 216 may include a door with a handle, a tray attached to the door 228, and a rail 232 on which the tray 228 may be slidably inserted into and out from the interior cavity of the device 102. A dispensing cup 226, into which a supplement dose is dispensed, may be removably attached to the tray 228 by any of a number of ways. In a preferred embodiment, the cup 226 may be attached to the tray via a keyed hole, as shown in FIG. 2E. The cup may be single use, disposable, or multi-use. The tray 228 may be configured to be removable for cleaning. The door may have a handle for manual operation by a user, or may open and close by push-button activation, or may open and close automatically, such as by motorized operation, according to the software of the system. As can be seen in FIG. 2G, the drawer 216 when fully inserted into the opening aligns the cup 226 below an optional chute from which ingredients from a particular ingredient cartridge 234 are dispensed. Moreover, one or more motors 236 may cause the cartridge 234 to dispense the ingredient into the cup at the desired dose, e.g., one, two, or three pills or other units, etc. The plurality of cartridges 220 may be mounted on a carousel, which is rotated by the device 102 so that the desired ingredient is oriented and dispensed into the cup 226. As discussed above, the device 102 may include status lights 230, which display the function of the device. For example, a first color may represent mixing or preparation, and a second color may represent that the formulation is ready.

Figure 2A:
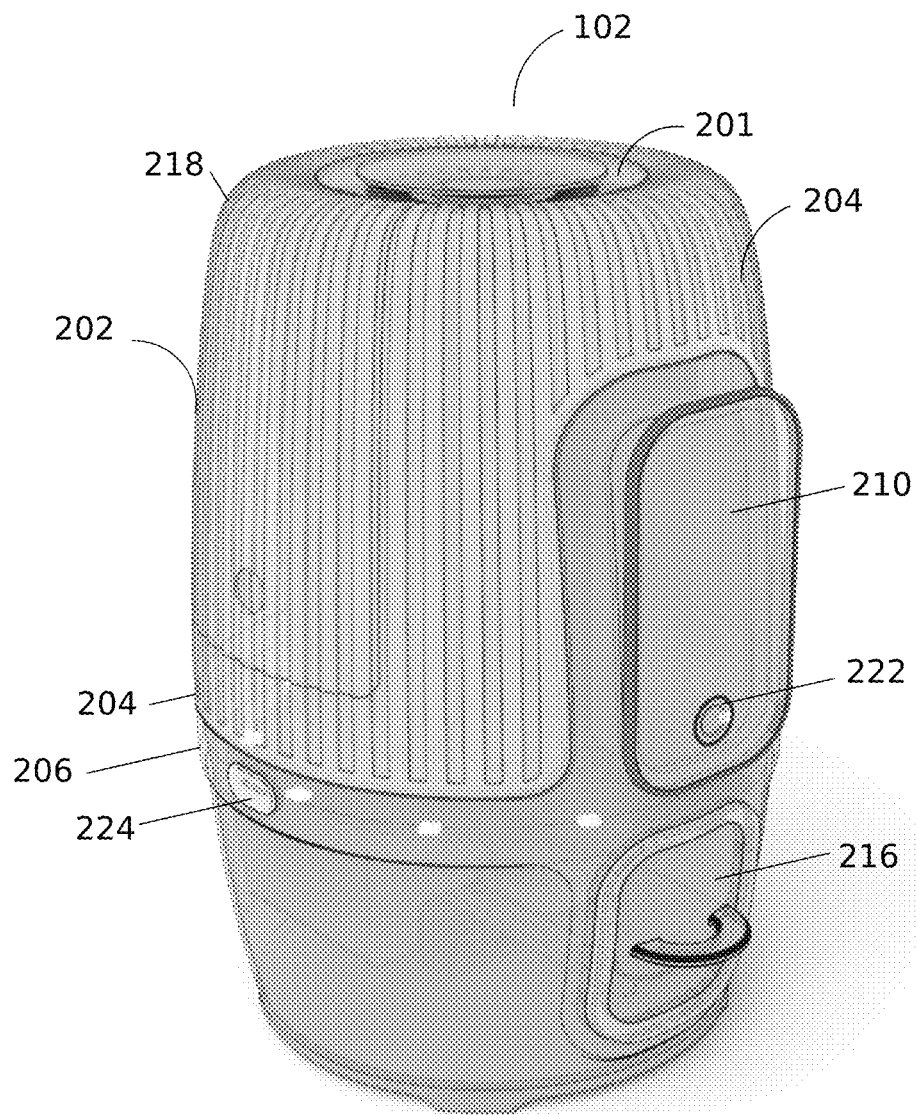
FIGS. 2A-2I illustrate a supplement delivery device in accordance with an exemplary embodiment of the devices disclosed herein.
Figure 2B:
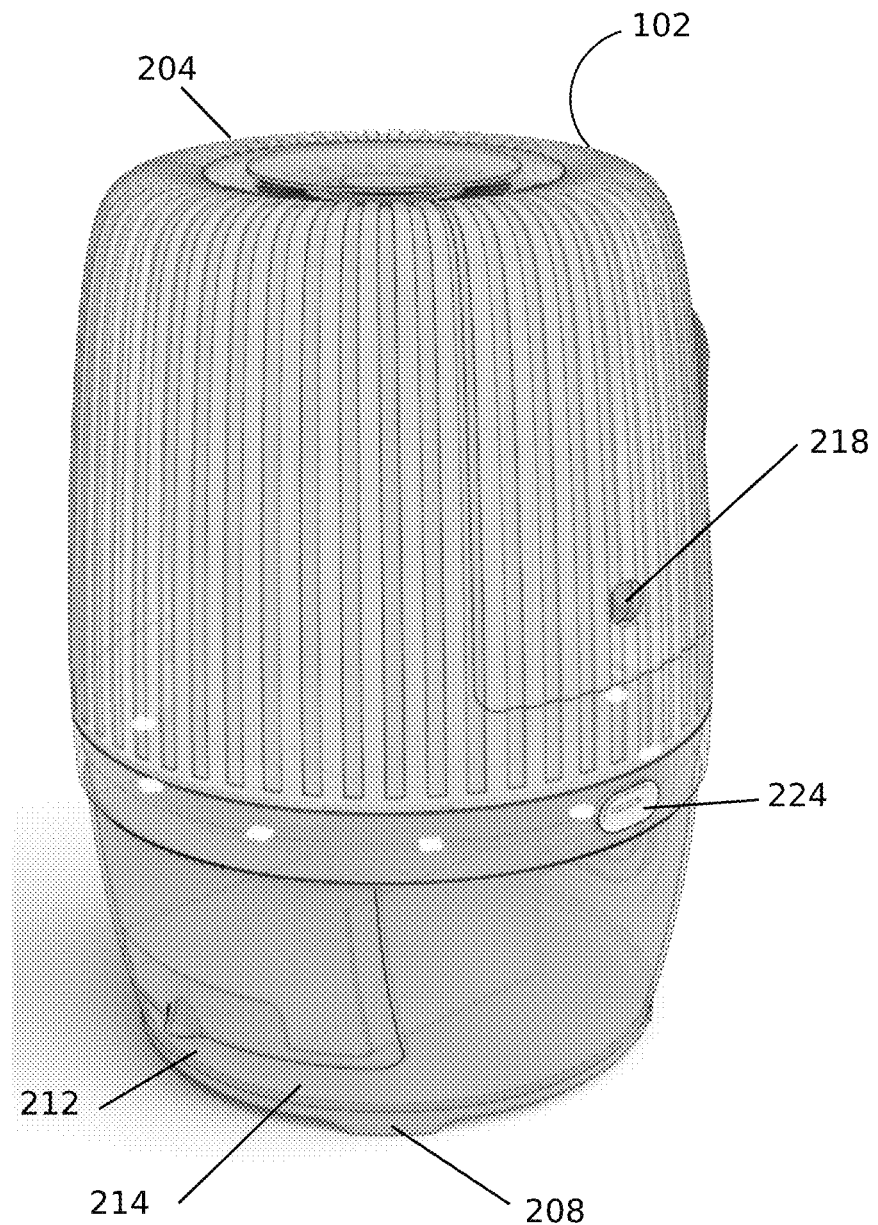
Figure 2C:
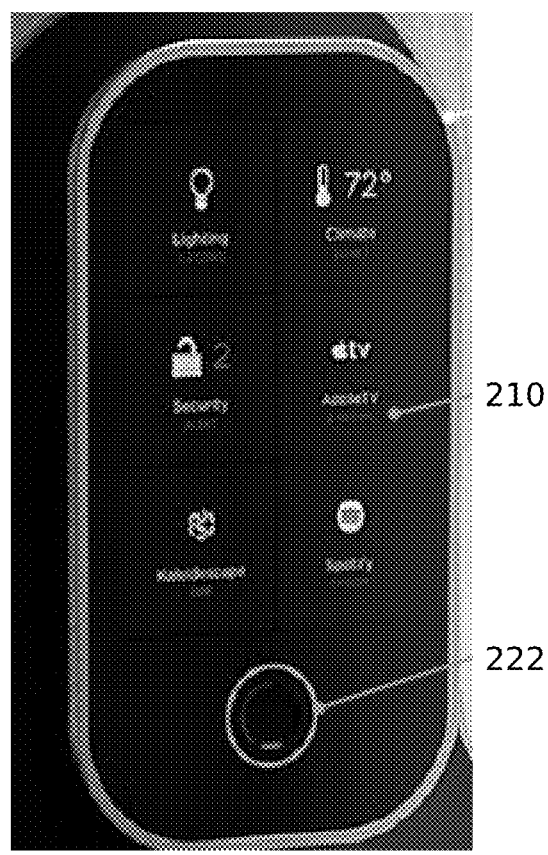
Figure 2D:
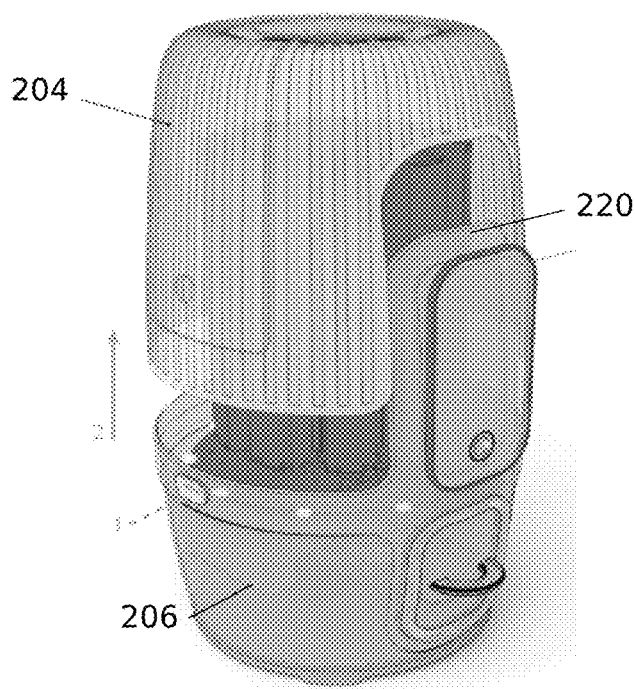
Figure 2E:
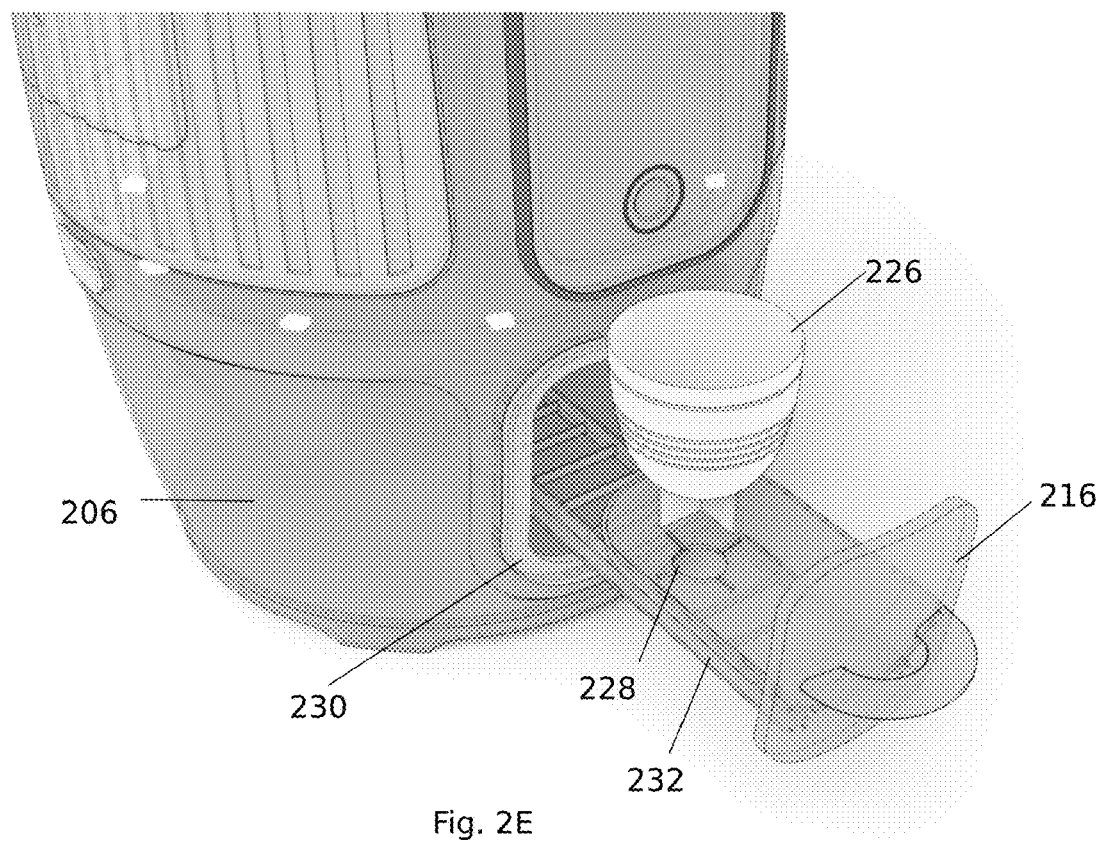
Figure 2F:
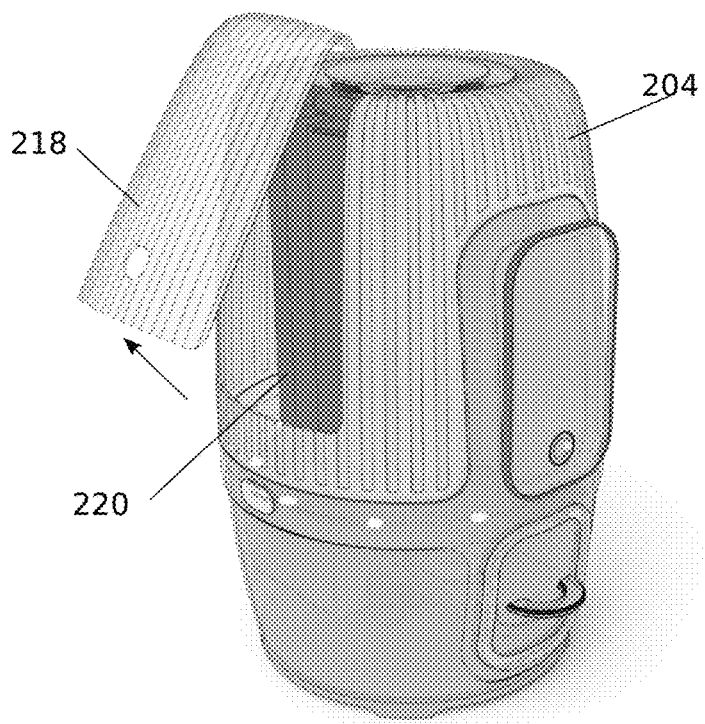
Figure 2G:
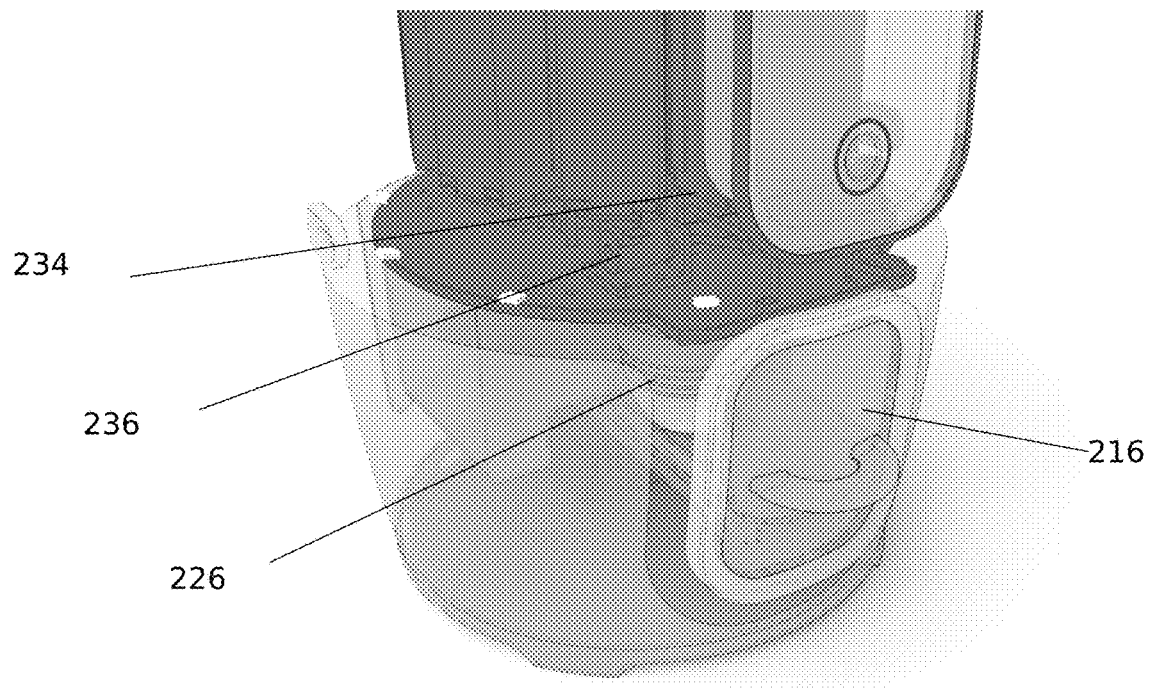
Figure 2H:
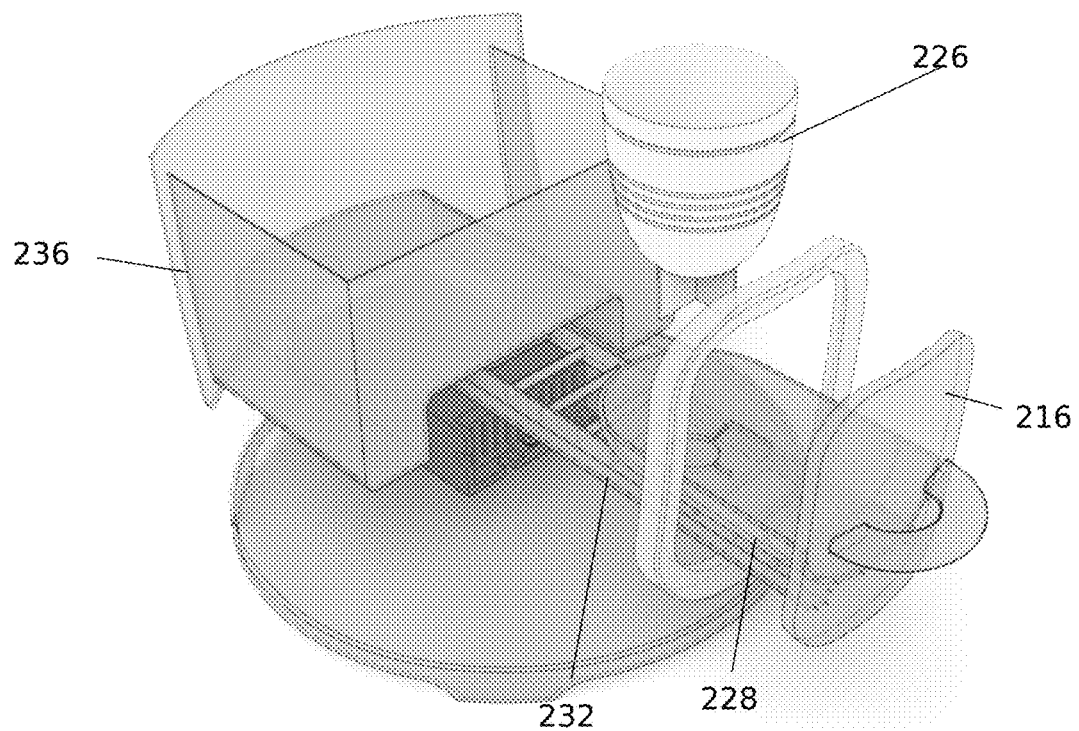
Figure 2I:
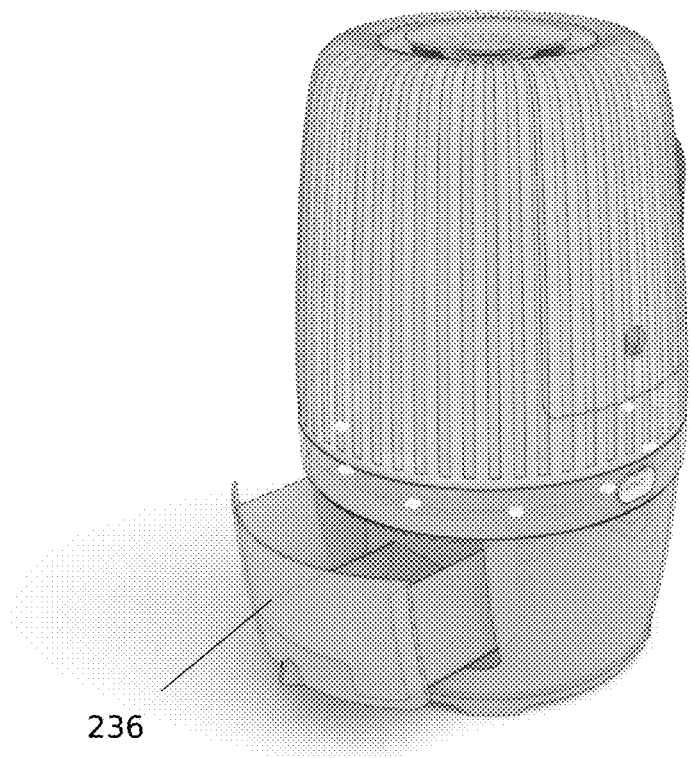

In a preferred embodiment, a second opening is provided on the rear exterior surface of the base 206, as shown in FIG. 2I. The opening provides access to the interior space of the device base 206 and further provides a receptacle for ejected/spent cartridges/blister packs by the system for removal and disposal. The receptable may be a drawer 236 having a handle for manual operation by a user, or may open and close by push-button activation or may open and close automatically, such as by motorized operation, according to the software of the system. The relationship between the front and rear drawers are shown in FIG. 2H, which depicts the front and rear drawers on opposite ends of the base section, with the sliding axis (direction of the sliding movement) essentially parallel. Moreover, the rear drawer 236 may have a recess or channel at the bottom thereof to accommodate the front drawer rail, as shown, and preferably the power supply.

In a preferred embodiment, the top, bell shaped section 204 of the device 102 defines an interior space in which the cartridges and cartridge/blister pack dispensing mechanism are located. The top section is preferably removable detachably from the base section by means of release buttons holding the bell section to the base, as discussed above. Release of the sections from each other provide access to the cartridge dispensing mechanism. The bell section 204 may also have a sliding door 218 which provides access to the interior space for cartridge replacement. The bell section 204 may also have an opening for ventilation and a cover or grille to cover the ventilation opening 201 at the top of the section 204.

In a preferred embodiment, the device includes a touch screen display 210 as shown in FIG. 2C, which may be mounted on the top section 204, base section 206, or both.

The display 210 allows a user to interface with the system 100 and/device 102. The display 210 may provide for access to other devices on the network, for example, to control a home thermostat, home lighting, video and audio streaming devices and services (e.g., Apple TV® and Spotify®), home security, and kaleidoscope.

In one embodiment, the display 210 or the device 102 generally provides secure access to the functionality, based on, for example, a password or biometric ID, such as with fingerprint sensor 222. Once granted, the device 102 provides access to functionality using a menu of selectable functions. An exemplary hierarchical menu is provided in table A. In one embodiment, the first hierarchy includes a user area, blister area, release plan, and/or system setup. In the user area, the user is preferably provided an interface screen for the user to select, add and/or remove users from the device 102. Adding users may be accomplished with a QR or other code provided to the user via the remote severs 112, for example, to a client device such as a smart phone. The user area may further provide usage data, for example, for the past two days, and planned usage (e.g., the formulation for the next dose, next several doses, etc.). Finally, the user may have a selectable option to release the next dose now. In response, the system 100/device 102 may select ingredients and the desired dosage, mix, and dispense the formulation, on demand.

As discussed above, the device 102 includes a set of ingredients. Each of the ingredients is preferably provided in a cartridge and/or blister packs. In this regard, the menu may include functions relating to the ingredients. For example, the menu may allow the user to add, remove, and/or replace a cartridge/blister tube in a select bay. The device 102 preferably tracks the level of ingredients in the device 102/cartridge/blister tube. In this regard, the system provides a selectable button for displaying the level of ingredients.

In one embodiment, the system 100 allows users to create supplement plans for a desired time, e.g., next day, week, etc. In this regard, the device 102 allows the user to view past and future plans, and to the extent that real-time dispensing departs from the plans, the difference if any. Preferably, the user is provided a button that when selected causes the system to dispense the dose according to the selected plan.

TABLE A

System Menu

1. User Area
1. Add-Remove-Select
i) Add: show QRcode → confirm User
ii) Remove: Select User → Confirm Remove
iii) Select: show point 2, point 3, point 4 (below)
2. Shot Released in past 2 days
3. Next 2 days plan
4. Release Shot Now → Select User → Select Shot from his/her plan
2. Blister Area
1. Add: select bay → insert blister tube
2. Remove: select bay → remove blister tube
3. Replace: select bay → remove the old one and insert the new one
4. Check quantity: show total or single type quantity
3. Release Plan
1. Check General Plan (show daily plan with all the connected users)
2. Check User Plan:
i) Select User
ii) check past 2 days plan
iii) check next 2 days plan
3. Release Shot now
i) Select User → Select Shot from his plan
4. Setup
1. Display TABLE A-continued System Menu 2. Network
3. Time and Data
4. Language
5. Clean
6. Reset In a preferred embodiment, the device 102 is about 27 cm in diameter and 42 cm height, with a cylindrical shaped body that tapers at the top and bottom. However, the device may be of any shape and size suitable for performing the functions described herein.

Figure 3A:
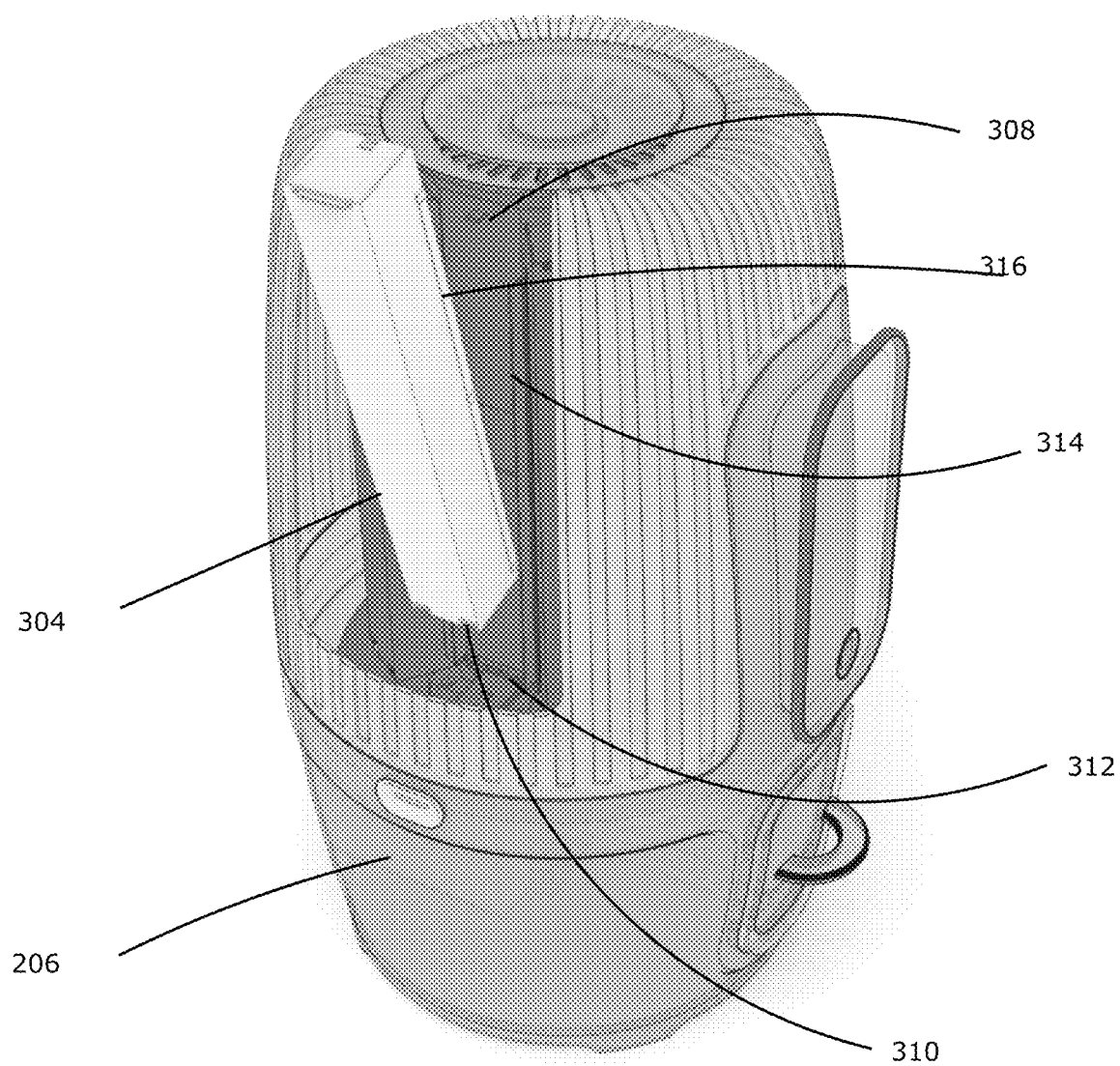
FIGS. 3A-3C illustrate various views of a cartridge/cartridge mechanism for use with a supplement delivery device in accordance with an exemplary embodiment of the devices disclosed herein.
Figure 3B:
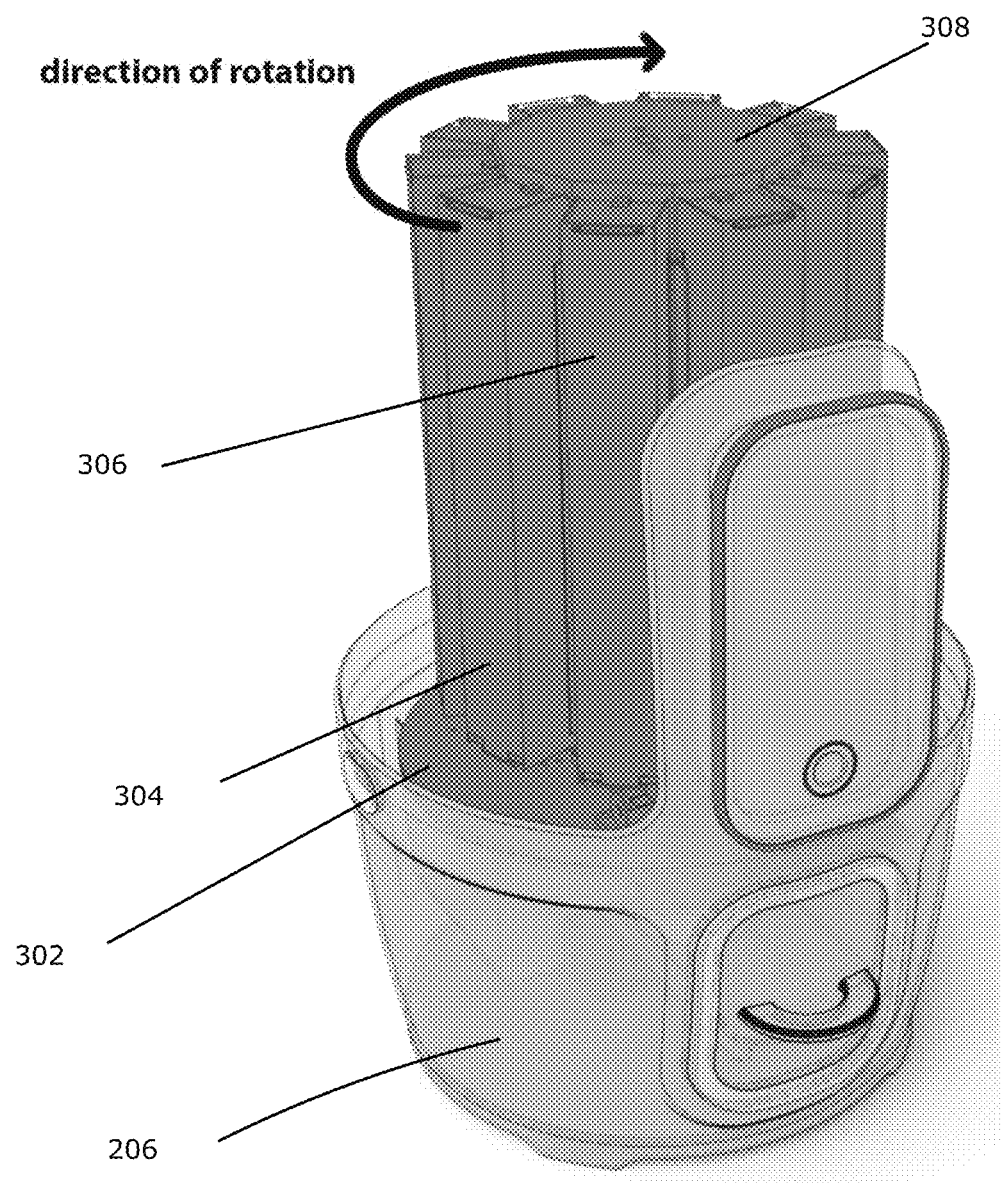
Figure 3C:
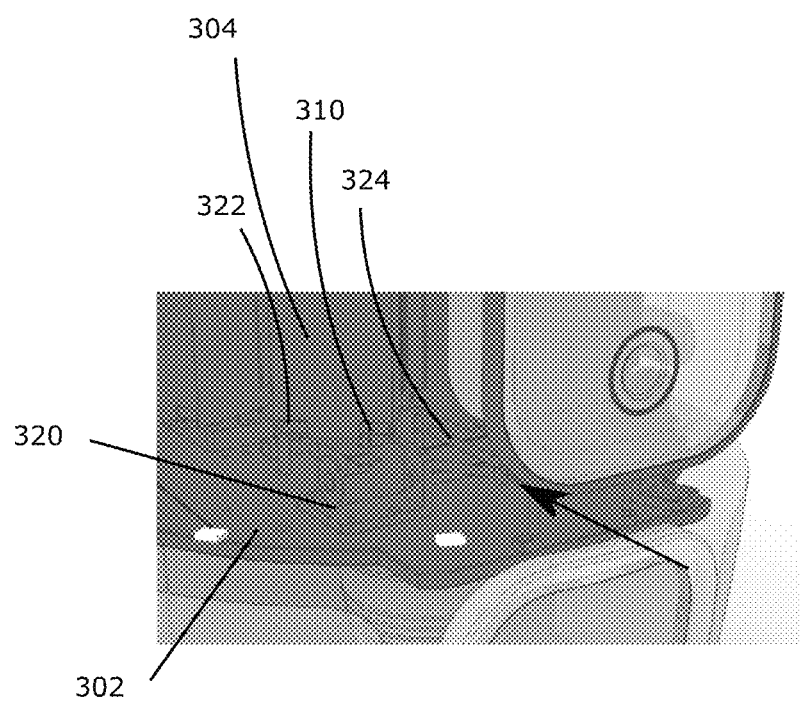

Referring now to FIGS. 3A-3C, an exemplary embodiment for the cartridges of the personal supplement supply system is shown. In a preferred embodiment, the ingredients/supplements are supplied in pre-packaged disposable or refillable cartridges 304. The cartridge may be in any form suitable for performing the functions described herein. The cartridge 304 may comprise a rigid storage housing, a soft housing, or no housing at all. The ingredient may be in single-serving blister packs 310, stacked vertically within the cartridge 304, or may be dispensed or released from an ingredient reserve into single-serving amounts. In one embodiment, the cartridge 304 is an elongated element, with a generally square or rectangular cross section, that fits and removably engages within a channel 314 on the carousel 308. The cartridge 304 has a top and a bottom that define a tubular space within the cartridge to house the ingredient/blister packs. In this regard, the ingredients/blister packs may be inserted through an opening in the top of the cartridge 304 and may exit from an opening in the bottom of the cartridge 304. The opening in the bottom of the cartridge 304 may align with a corresponding opening 312 in the carousel 308 and/or base 302. Opening 312 feeds toward a dispensing mechanism, as discussed further below, which dispenses the ingredient/blister pack into the cup 226. As discussed above, the device 102 may house a set of cartridges 304, 306, preferably all removably mounted to a carousel 308. The carousel 308 is further rotatably mounted on a base 302. The cartridges 304, 306, etc., may be located radially about a central axis of the carousel such that rotational movement by the device 102 of the carousel 308 selectively places the desired cartridge in a position for feeding ingredients from the cartridge into a dispensing mechanism.

In one embodiment, as shown in FIG. 3C, the device 102 includes a cartridge/blister pack feed mechanism, which includes a motor 320 coupled to feed armature 324. The feed armature may be any mechanism for providing lateral movement in the direction of the center of the carousel, including a solenoid or a crank/connecting rod assembly. As can be seen at the bottom end of the cartridge 304 one or more openings 322 provide access to blister pack 322 stacked within the cartridge 304. The device 102 rotates the carousel 308 so that cartridge 304 and more specifically blister pack 310 is placed in-line with the feed armature 324. When actuated, feed armature 324 pushes blister pack 320 inwardly, via the access provided with opening 322, toward the center of the carousel, preferably to a mechanism that opens the blister pack 310, as discussed below. The armature 324 retracts and the next blister pack 310 in the cartridge 304 lowers within the cartridge housing to be next in line for dispensing.

In a preferred embodiment, each ingredient or supplement is supplied in a separate cartridge. Each cartridge may be labeled or identified using a coding system, such as a bar code or QR code, to enable the system to recognize and monitor each ingredient. Moreover, each cartridge preferably includes a plurality of individual blister packs, each containing the desired ingredient. It is also possibility that multiple ingredients can be included within a single blister pack cartridge so that the range of ingredients or combinations can be extended without the requirement for adding a larger carousel. This may be achieved with a directional blister pack so that the system may know or otherwise track the location of the desired blister ingredient location on the blister pack.

The cartridge housing may contain a window with a "blisters" or "blister pack remaining" index or any means for physically viewing the number of doses/blister packs remaining in the cartridge housing.

In one embodiment, the cartridge may be a spooled perforated single-serving blister pack. In a preferred embodiment, each cartridge may contain 60 aluminum foil blister packs containing 0.5 grams of ingredients (e.g. supplements), though a cartridge may contain any number of units of any volume suitable for performing the functions described herein. The cartridge may also be in the form of a tower, as show, with a plurality of blister packs therein.

In one embodiment, the cartridge carousel containing a plurality of cartridges, each containing an ingredient, is configured to rotate in response to instructions/formulations received from the server. The carousel may rotate to present a specific cartridge containing a desired ingredient to the fee/dispensing mechanism. The carousel may contain a hammer-action blade for cutting the blister pack to dispense the contents therefrom. The carousel may also contain a chute to feed the dispensed contents by gravity to the dispensing cup 226.

Figure 4A:
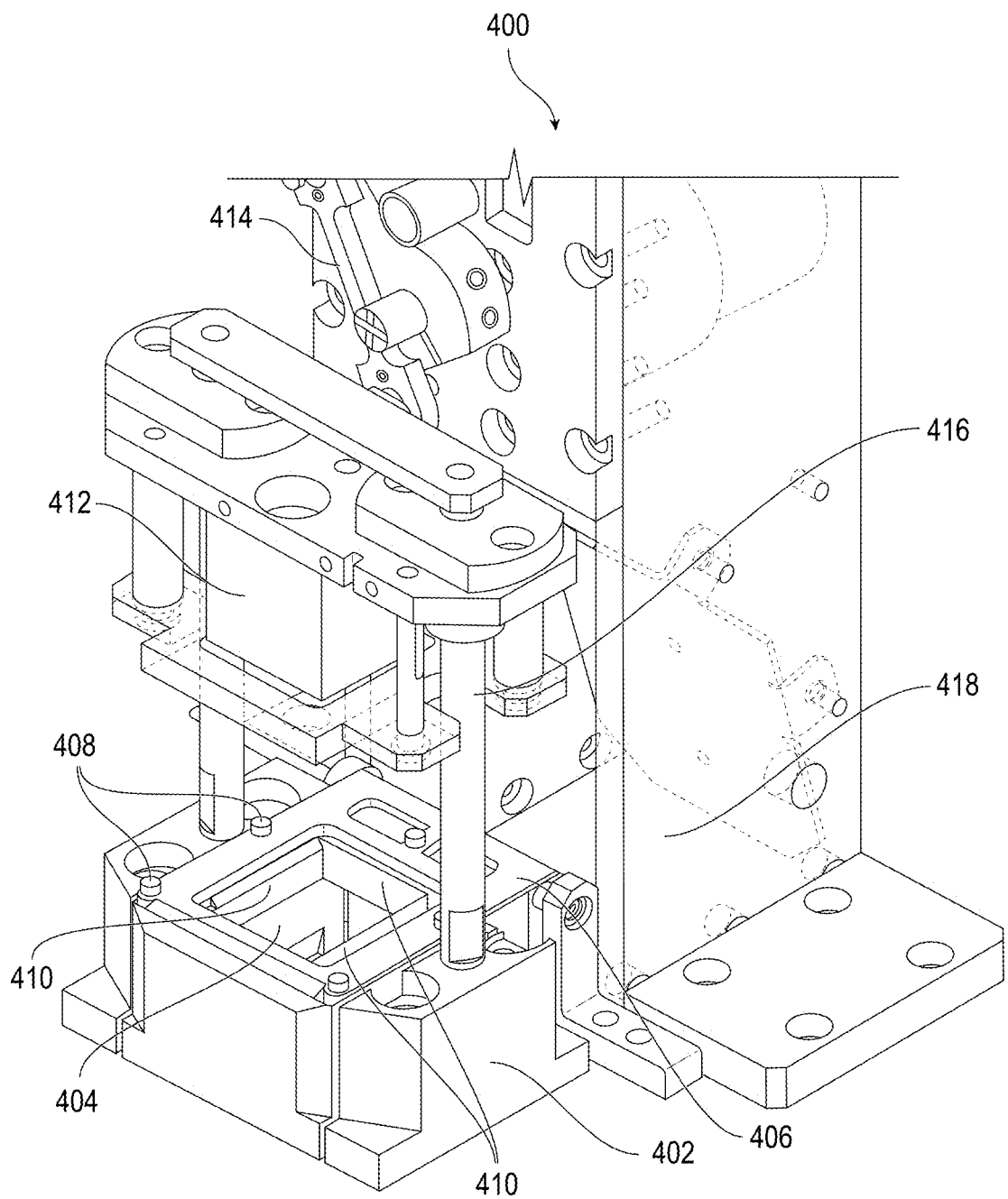
FIGS. 4A-4C illustrate dispensing mechanisms for use with a supplement delivery device in accordance with an exemplary embodiment of the devices disclosed herein.
Figure 4B:
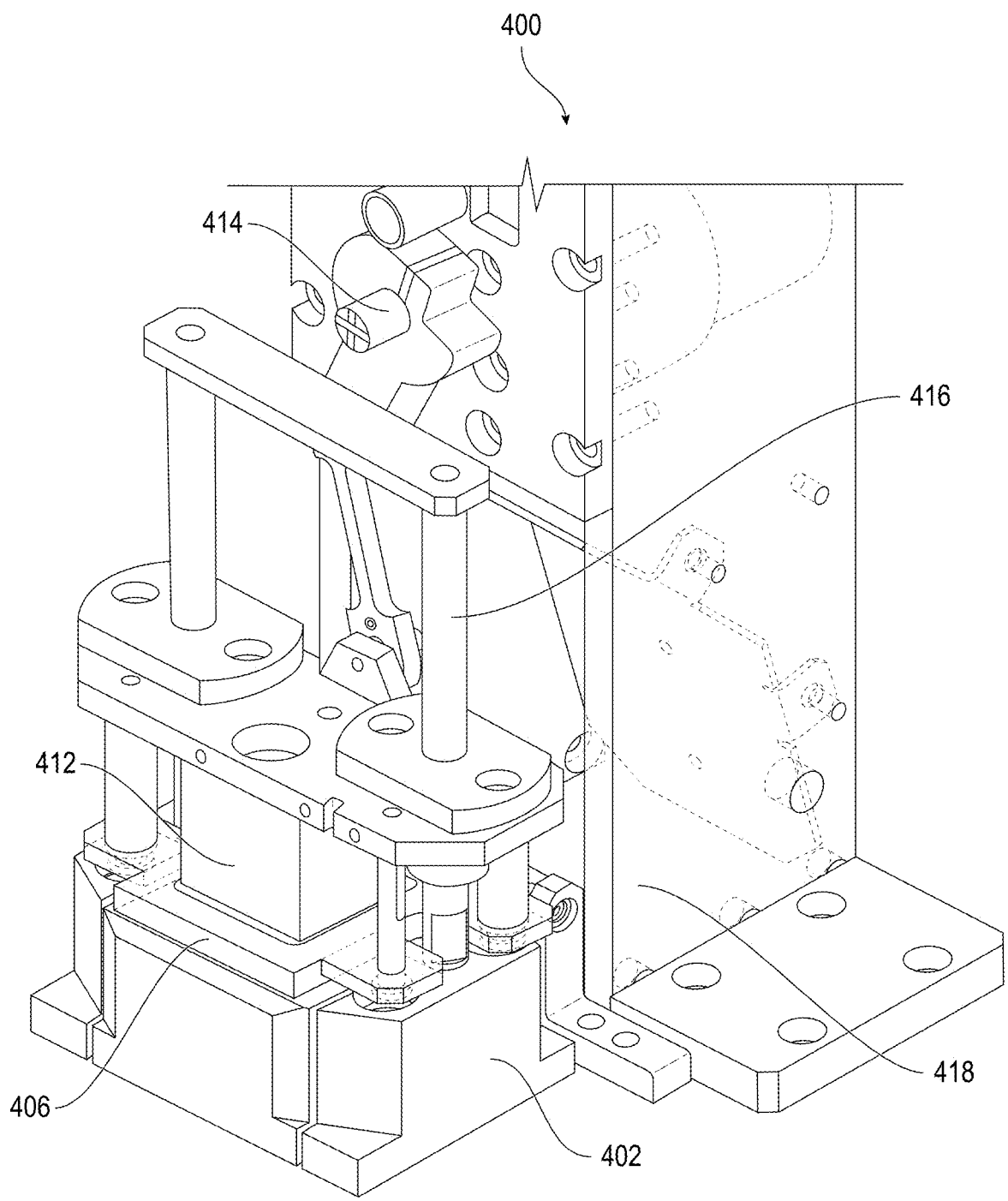
Figure 4C:
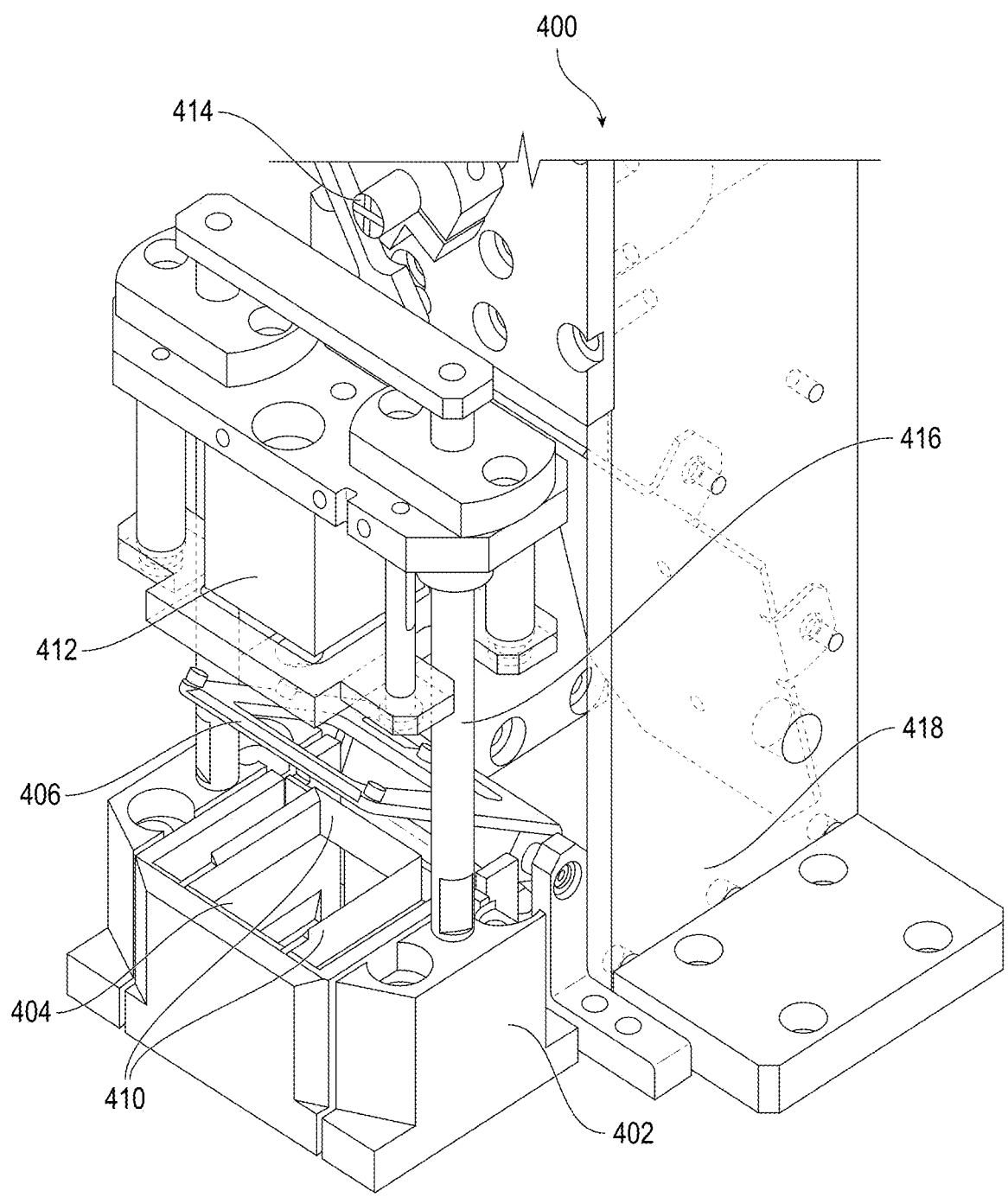

Referring to FIGS. 4A-4C, the dispensing mechanism 400 is generally disposed on the base 302 and centrally located within the carousel 308. The dispensing mechanism includes base 402 with an opening 404 therein located over the cup 226. Within the opening 404, the base 402 includes a plurality of blades 410, preferably partially surrounding the perimeter of the opening 404. For example, with a generally square opening 404, the base 402 may be equipped with blades 410 on three of the four sides. The mechanism 400 may further include blister pack retention plate 406, preferably pivotally coupled to the base 402. The retention plate 406 has an opening therein that coincides with the opening 404 in the base 402 and preferably includes a plurality of alignment pins 408 extending upward from the face of the plate 406. The alignment pins generally create a channel with an opening at the front end of the plate 406 so that blister packs may be fed by the feed mechanism into the channel and so that the blister pack contents may be located over the openings in the plate 406 and base 402. Once the blister pack is located into the channel, a hammer mechanism 412 may press the blister pack downward toward the knives 410, thereby cutting the blister pack to expose the content thereof. The content of the blister pack will then drop into the cup 226 located below the openings 404. In one embodiment, the hammer mechanism includes a crank and motor assembly 414 that moves the press portion vertically via one or more vertical posts 416, between a raised position (FIG. 4A) and a lowered position (FIG. 4B). Finally, the spent blister pack may be ejected from the retention plate 406, for example, by pivoting plate 406 so that the spent blister pack falls into the drawer 236.

In operation, in a preferred embodiment, the personal supplement delivery device 102 may be accessible via a software app on a user's connected device, e.g., tablet or smart phone. The software app may be configured to scan a code unique to a user's personal supplement delivery device, enabling the system to recognize the user and/or the device. The device 102 may instruct the user to place his finger on the device touchpad to capture the user's fingerprint and start the registration. The device 102 may also instruct the user to enter a preferred PIN, to allow a choice of access. In a preferred embodiment, the system may support multiple subscriber accounts and profiles at same time.

In a preferred embodiment, the software app may send a user a reminder, such as through a push notification, that it is time to take their "dose". The user may access the device and enter their PIN or fingerprint. Once successfully identified by the device 102, the device 102 may communicate with the server 112 and begin to prepare the appropriate dose for the user in response to instructions/formulations received from the server 112. A dose may include one or more ingredients/supplements at various dosages. The server 112 may instruct the device 102 to dispense ingredients from the respective cartridges containing the required ingredients for the dose, e.g., dispense the ingredient combination A, B, and D as contained in cartridges 2, 4, and 7, respectively. Moreover, the server 112 may instruct the device with respect to the dosage of each of the ingredients, e.g., one, two, three, etc. units, or 0.5 grams, of ingredient A. The cartridge carousel may rotate axially and presents the required cartridge based on the formulation from the server 112. The blister pack may be cut by blades using a hammer action, causing the contents to be gravity-fed to the dispensing cup via a chute. While one embodiment for dispensing ingredients from the cartridges is described, any number of means known to one of ordinary skill in the art may be used to perform the functions described herein.

On demand, real-time formulations can be prepared using the artificial intelligence cloud service/AI engine, which can be queried using voice commands and can provide information on the user's personal status, check and communicate the user's biometrics, and request a specific supplement based on information provided to the artificial intelligence service and interaction with the user.

In a preferred embodiment, the system 100 formulates a personalized single "shot" or a schedule of shots that can be prepared by the delivery device 102 according to a variety of data sources, including the user's personal profile created by the user and shared with the system, a DNA, blood, and/or microbiome analysis, the user's responses to health assessment questionnaires/surveys, the user's activity, and other data discussed herein, such as objective biometric data, gathered by other devices that are connected via a communication network to the system, such as a smartphone or smartwatch. This data is preferably provided to the AI engine to be compiled and used to perform the functions of the system discussed herein.

In a preferred embodiment, the supplement dose is customizable by the system based on the user's biometric data. The AI engine collects biometric information from the user and outputs a custom supplement dose for the user in real time. The biometric data may come from a wearable device or smart device connected to the network, such as a smartphone or smartwatch configured to collect a user's biometric data, such as sleep, heart rate, extrapolated blood pressure, glucose levels, etc.

In a preferred embodiment, the AI engine uses the user's source data provided by the user's health assessment questionnaire and bodily function readings gathered by a wearable device that is capable of detecting biometric information. The bodily function readings, combined with the user's health records information, may be used to deduce a user's profile. For example, if the user is male, over age 50, with a typical blood pressure range of 134/84, then they are determined to have moderate hypertension. Heart rate variability (HRV) may be used to calculate the user's energy level. If a user is determined to have low energy, then this may be considered as an important factor for that user's supplement selection.

For example, it is known that biotin, B12 vitamins, taurine, caffeine, and many other supplement ingredients can significantly help the body restore its physical and mental energy. Based on the user's available information, the AI engine may select ingredients that, according to the recommended daily allowance table inputs, will help the body to address specific issue identified. Using this as well as other information, the AI engine may formulate and outputs a custom supplement dose for the user.

As the wearable device continuously collects data from the user, the system will preferably recognize that the user's personalized supplement dose (SmartShot™) has been produced and presented to the user. It is assumed that the user has taken his or her personalized supplement, so it will attempt to calculate, using machine learning and deep learning, the correlation between the supplements in the personalized supplement and the change in user's data. If, for example, it is found that the user's energy level has recovered and improved in a specific time with a specific selection of the ingredients or supplements, the AI engine will learn what works best for this user. It will also compare this result with other users, to see if that specific combination of supplements can be optimized and still remain effective. Consequently, when a similar situation arises for that user, instead of selecting the RDA amounts, it may choose an optimized supplement combination and may assess if it remains effective for that user, thereby enabling automatic feedback. If, over time, the user's energy levels remain within normal levels, then the personalized supplement will not include any unnecessary supplements or vitamins.

For example, the system will provide a particular supplement if there is a lack of sleep, such as melatonin. If the user's blood pressure is high, the system may provide a supplement correlated to produce desired results. If there is no set algorithm, the system may start with a generic algorithm and learn how to compensate for the particular user. The AI engine may also compensate for athletic users vs. sedate users, etc.

In a preferred embodiment, the system 100 can be operated by voice interactive command technology, wherein the system communicates with the user, queries the user, receives voice response data from the user in response to the query, and determines a treatment option for dispensing a supplement dose according to the data collected and subject to dosage restrictions. Examples of the system's voice interactive command technology protocol are provided below. In the examples, the AI engine may be called Oracle™ and the dispensed dose may be called SmartShot™.

In one embodiment, as shown in Example 1, the AI engine may provide a health status update and report based on information collected about the user.

Example 1

User: Hey, Oracle.
Oracle: Hi <Username>, how may I help you?
User: Can you update me on my health status today?
Oracle: Sure. Based on my last record at 8:30 am, Jun. 5, 2019, your heart rate is 84 beats per minute, your breath rate 14 breaths per minute, your blood pressure is 134 systolic and 84 diastolic, your energy level is very good, and it looks like your mood is happy. Unfortunately, last night your quality of sleep was not good. You should go to sleep a little earlier, and please do not eat too much or drink alcohol before going to bed. Do you want me to send the report to your email?
User: Yes, please.
Oracle: Report sent.

In one embodiment, as shown in Example 2A, the AI engine may cause to be dispensed a supplement dose in response to a health complaint of the user.

Example 2A

User: Hey, Oracle.
Oracle: Hi <Username>, how may I help you?
User: I have a back pain today.
Oracle: Oh, very sorry to hear that. How is your back pain? Can you describe the intensity? Is it just a little sore, quite intense, or very intense?
User: Very intense.
Oracle: Do you want me to call a doctor or a guardian in your list or do you want to try one of my SmartShots™?
User: Please prepare a shot for me.
Oracle: Ok, well, I am preparing a SmartShot™ to help you with your back pain. Please wait a moment . . . Your SmartShot™ is ready. Please press start now or when you are ready to take it.

In one embodiment, as shown in Example 2B, the artificial intelligence cloud service may decline to dispense a supplement dose in response to a health complaint of the user because the user has exceeded the daily recommended dose for a supplement for that day.

Example 2B

User: Please prepare a shot for me.
Oracle: I am sorry <Username>, according to your instructions, I should prepare a SmartShot™ for you based on acetaminophen. Unfortunately, the amount of acetaminophen you have taken today exceeds your daily recommended dose. Would you like me to call a doctor or a guardian?

In one embodiment, as shown in Example 3, after the AI engine has received information that the SmartShot™ has been dispensed, in about two hours it will send a notification to the user via the device or smart phone asking for feedback on their status. If the user's status has not improved, the artificial intelligence cloud service may suggest another supplement dose or state that the daily recommended dose has been reached.

Example 3

Oracle: Hey <Username>, how do you feel now?
User: Very good, thanks. [or] I am still in pain.
Oracle: Do you want to try one more SmartShot™? [or] I am sorry to hear that but I can't prepare any more shots today because your daily recommended dose has been reached.

Doses may be dispensed as required by the supplement plan prepared by the AI engine (mornings and evenings and pre-mealtime if the user takes) or on demand, where the user can select the plan (as discussed above) and request a specific dose to be prepared by the device. Supplement requirements for people who fall into certain categories can be grouped initially and be provided with a general plan based on, for example, body type, how well they sleep, their stress levels, etc. Thereafter, the additional supplementation required may be calculated based on actual measurements (as discussed herein) and/or anecdotal/survey evidence, including with regard to how well the user sleeps, stress levels, etc.

Thus, while there have been shown and described and pointed out fundamental novel features of the personal supplement supply system as applied to preferred embodiments thereof, it will be understood that various omissions and substitutions and changes in the form and details of the personal supplement supply system illustrated, and in their operation, may be made by those skilled in the art without departing from the spirit of the disclosure. For example, it is expressly intended that all combinations of those elements and/or method steps which perform substantially the same function in substantially the same way to achieve the same results are within the scope of the application. It is the intention, therefore, to be limited only as indicated by the scope of the claims appended hereto.

The invention claimed is:

1. A personal supplement supply system comprising:
    a delivery device comprising:
        a housing having a plurality of cartridges removably attached to a base located within the housing, each of the plurality of cartridges storing therein at least one dispensable ingredient;
        a cylindrical top section defining an interior space in which the plurality of cartridges reside, the cylindrical top section being removably detachable from the base located within the housing, the cylindrical top section including a closable door providing access to the interior space in which the plurality of cartridges reside, the door running vertically from a top part of the cylindrical top section to a bottom part of the cylindrical top section;
        a carousel rotatably mounted about an opening in the base, the carousel providing a plurality of channels to receive the plurality of cartridges; and
        a processor coupled to computer memory, the computer memory having software stored thereon that when executed causes the delivery device to dispense the at least one dispensable ingredient from each of the plurality of cartridges in accordance with a bio-informed plan personalized for a user of the delivery device.

2. The supplemental supply system of claim 1, wherein the ingredient comprises at least one dietary supplement.

3. The supplemental supply system of claim 1, wherein each of the plurality of cartridges store the dispensable ingredient in a plurality of blister packs and wherein each of the plurality of cartridges are configured to be refilled with blister packs.

4. The supplemental supply system of claim 3, wherein at least one of the plurality of cartridges or the plurality of blister packs are addressed with a code, and wherein the delivery device is configured to recognize ingredients in blister packs and track consumption thereof based on said code.

5. The supplemental supply system of claim 1, the delivery device further comprising a communication unit, the delivery device therewith operable to communicate with at least one mobile device over a communication network and receive therefrom user specific biometric data, wherein the personalized bio-informed plan is determined based at least in part on the user specific biometric data received from the mobile device.

6. The supplement supply system of claim 5, wherein the user specific biometric data comprises objective health data.

7. The supplement supply system of claim 5, wherein the user specific biometric data comprises subjective health data.

8. The supplement supply system of claim 5, wherein the software when executed further causes the delivery device track consumption by the user of the at least one dispensable ingredient and update the bio-informed plan personalized based on said consumption and based on changes to user specific biometric data after a start of said consumption.

9. The supplement supply system of claim 5, wherein at least one of the mobile device or the delivery device are operable to communicate biometric data to a remote server and wherein the remote server communicates the personalized bio-informed plan determined based on the biometric data by the server to the delivery device.

10. The supplement supply system of claim 9, wherein the server executes an artificial intelligence cloud service and wherein the cloud service determines the personalized bio-informed plan based on biometric reports from a plurality of users and a correlation of changes to biometric data with ingredient consumption.

11. The supplement supply system of claim 9, wherein the delivery device is operable to receive a request for a supplement via the delivery device, communicate the request to the server, and receive from the server the personalized bio-informed plan for the user in response to the request for the supplement.

12. The supplement supply system of claim 11, wherein the software when executed further causes the delivery device to track consumption by the user of the at least one dispensable ingredient, and wherein the bio-informed plan is personalized in real-time based on said consumption and based on changes to user specific biometric data over a preceding time period.

13. The supplemental supply system of claim 1, wherein the software when executed aligns an opening in a first one of the plurality of cartridges to a dispensing mechanism for dispensing a first ingredient and aligns an opening in a second of the plurality of cartridges to the dispensing mechanism for dispensing a second ingredient, the first and second ingredients dispensed based on the bio-informed plan.

14. The supplemental supply system of claim 13, wherein a removable cup is aligned with the opening in the base for receiving a mixture comprising the first and second ingredients.

15. The supplemental supply system of claim 14, comprising a rail slidably coupled to the housing, the cup removably attached to the rail.

16. The supplemental supply system of claim 13, wherein each of the plurality of cartridges include at least one blister pack and wherein the dispensing mechanism comprises armature that feeds blister packs over the opening in the base.

17. The supplemental supply system of claim 16, wherein the opening in the base comprises at least one blade, the dispensing mechanism comprising a hammer mechanism that presses the at least one blister pack onto the at least one blade for cutting the blister pack and releasing ingredients therefrom into a cup.

18. The supplemental supply system of claim 16, wherein the dispensing mechanism comprises a retention plate pivotally coupled to the base, the retention plate having an opening therein that coincides with the opening in the base and a plurality alignment pins that align blister packs fed thereto over the opening in the retention plate, the retention plate operable to eject spent blister packs into a drawer located within the housing.

19. A personal supplement supply system comprising:
a delivery device comprising:
   a housing having a plurality of refillable cartridges removably attached to a base located within the housing, each of the plurality of cartridges storing therein at least one dispensable ingredient in a blister pack;
   a cylindrical top section defining an interior space in which the plurality of cartridges reside, the cylindrical top section being removably detachable from the base located within the housing, the cylindrical top section including a closable door providing access to the interior space in which the plurality of cartridges reside, the door running vertically from a top part of the cylindrical top section to a bottom part of the cylindrical top section;
   a carousel rotatably mounted about an opening in the base, the carousel providing a plurality of channels to receive the plurality of cartridges;
   a processor coupled to computer memory, the computer memory having software stored thereon that when executed causes the delivery device to:
      dispense the at least one dispensable ingredient from each of the plurality of cartridges in accordance with a bio-informed plan personalized for a user of the delivery device,
      track consumption by the user of at least first and second dispensable ingredients; and
   a communication unit, the delivery device therewith operable to:
      communicate with at least one mobile device over a communication network and receive therefrom user specific biometric data,
      communicate with at least one server the user specific biometric data and said consumption, wherein the personalized bio-informed plan is determined based at least in part on the user specific biometric data, and
      received from the at least one server for execution bio-informed updated bio-informed plans based on said consumption.

20. The supplement supply system of claim 19, wherein the server executes an artificial intelligence cloud service and wherein the cloud service determines the personalized bio-informed plan based on biometric reports from a plurality of users and a correlation of changes to biometric data with ingredient consumption.

21. The supplemental supply system of claim 19, wherein the software when executed aligns an opening in a first one of the plurality of cartridges to a dispensing mechanism for dispensing the first ingredient and aligns an opening in a second of the plurality of cartridges to the dispensing mechanism for dispensing the second ingredient, the first and second ingredients dispensed based on the bio-informed plan.

22. The supplemental supply system of claim 21, comprising a rail slidably coupled to the housing and a removable cup for receiving dispensed ingredients removably attached to the rail.

23. The supplemental supply system of claim 22, wherein each of the plurality of cartridges include at least one blister pack and wherein the dispensing mechanism comprises armature that feeds blister packs over the opening in the base.

24. The supplemental supply system of claim 23, wherein the opening in the base comprises at least one blade, the dispensing mechanism comprising a hammer mechanism that presses the at least one blister pack onto the at least one blade for cutting the blister pack and releasing ingredients therefrom into the cup.

25. The supplemental supply system of claim 24, wherein the dispensing mechanism comprises a retention plate pivotally coupled to the base, the retention plate having an opening therein that coincides with the opening in the base and a plurality alignment pins that align blister packs fed thereto over the opening in the retention plate, the retention plate operable to eject spent blister packs into a drawer located within the housing.

* * * * *